(12) United States Patent
Johnson et al.

(10) Patent No.: US 8,105,315 B2
(45) Date of Patent: Jan. 31, 2012

(54) BREAK-AWAY HEMOSTASIS HUB

(75) Inventors: Eric T. Johnson, Temecula, CA (US); Christopher C. Andrews, Lake Elsinore, CA (US); Neil M. Becker, Fallbrook, CA (US); Gary L. Hague, Carlsbad, CA (US); Thomas L. Kindberg, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 137 days.

(21) Appl. No.: 11/860,854

(22) Filed: Sep. 25, 2007

(65) Prior Publication Data

US 2008/0108976 A1    May 8, 2008

Related U.S. Application Data

(60) Provisional application No. 60/864,895, filed on Nov. 8, 2006.

(51) Int. Cl.
  A61M 25/16    (2006.01)
  A61M 25/18    (2006.01)
  A61M 5/178    (2006.01)
  A61M 5/00    (2006.01)
  A61M 5/14    (2006.01)
  A61M 25/00    (2006.01)
  A61M 39/00    (2006.01)
  A61M 39/10    (2006.01)

(52) U.S. Cl. ............. 604/537; 604/164.01; 604/164.02; 604/164.12; 604/167.01; 604/167.02; 604/167.03; 604/167.04; 604/246; 604/256; 604/524; 604/533; 604/534; 604/535

(58) Field of Classification Search ............. 604/164.01, 604/164.02, 164.07, 167.01, 167.02, 167.04, 604/167.06, 246, 256, 264, 523, 533, 534, 535, 537, 539, 93.01, 164.12, 170.01, 170.02, 48, 905, 158, 160, 161, 164.05, 167.03, 524
See application file for complete search history.

(56) References Cited

U.S. PATENT DOCUMENTS 4,345,606 A    8/1982    Littleford
(Continued)

FOREIGN PATENT DOCUMENTS

EP    0631793    1/1995
(Continued)

OTHER PUBLICATIONS

International Search Report and Written Opinion of international application No. PCT/US2007/079396, mailed Jun. 5, 2008, 15 pp.

*Primary Examiner* — Kevin C Sirmons
*Assistant Examiner* — Shefali Patel
(74) *Attorney, Agent, or Firm* — Faegre & Benson LLP

(57) ABSTRACT

A breakaway hemostasis hub for a catheter or introducer sheath includes a splittable or separable housing, a seal within the housing, an actuator partially slidably disposed within the housing, a pair of spring retainer members in the housing each adapted to receive at least one spring, and a pair of actuator retainer members adapted to retain the seal, the actuator, and the spring retainer members in the housing. The actuator is operable to assume a closed position and an open position and includes a dilator member configured to dilate the seal when the actuator is in the open position. The hub is splittable or separable into two generally symmetrical sub-assemblies to facilitate cutting the catheter for retraction from the patient's body without displacing its payload.

21 Claims, 13 Drawing Sheets

U.S. PATENT DOCUMENTS

| | | | |
|---|---|---|---|
| 4,596,559 A | | 6/1986 | Fleischhacker |
| 4,626,245 A | | 12/1986 | Weinstein |
| 4,673,393 A | | 6/1987 | Suzuki et al. |
| 4,917,668 A | | 4/1990 | Haindl |
| 4,957,487 A | * | 9/1990 | Gerow ............................ 604/133 |
| 5,030,206 A | * | 7/1991 | Lander ...................... 604/164.12 |
| 5,108,380 A | * | 4/1992 | Herlitze et al. ................ 604/533 |
| 5,125,904 A | | 6/1992 | Lee |
| 5,176,652 A | | 1/1993 | Littrell |
| 5,195,980 A | | 3/1993 | Catlin |
| 5,273,546 A | | 12/1993 | McLaughlin et al. |
| 5,312,355 A | * | 5/1994 | Lee ............................... 604/160 |
| 5,397,311 A | | 3/1995 | Walker et al. |
| 5,405,323 A | | 4/1995 | Rogers et al. |
| 5,409,469 A | | 4/1995 | Schaerf |
| 5,441,504 A | | 8/1995 | Pohndorf et al. |
| 5,453,095 A | | 9/1995 | Davila et al. |
| 5,665,102 A | * | 9/1997 | Yoon ............................... 606/185 |
| 5,693,025 A | | 12/1997 | Stevens |
| 5,713,867 A | | 2/1998 | Morris |
| 5,741,233 A | | 4/1998 | Riddle et al. |
| 5,755,693 A | | 5/1998 | Walker et al. |
| 5,935,112 A | | 8/1999 | Stevens et al. |
| 5,951,518 A | | 9/1999 | Licata et al. |
| 5,989,232 A | * | 11/1999 | Yoon ............................... 604/523 |
| 6,024,729 A | | 2/2000 | Dehdashtian et al. |
| 6,228,060 B1 | | 5/2001 | Howell |
| 6,287,280 B1 | | 9/2001 | Lampropoulos et al. |
| 6,331,176 B1 | * | 12/2001 | Becker et al. ................. 604/533 |
| 6,352,521 B1 | | 3/2002 | Prosl |
| 6,488,674 B2 | | 12/2002 | Becker et al. |
| 6,562,049 B1 | | 5/2003 | Norlander et al. |
| 6,569,120 B1 | | 5/2003 | Green et al. |
| RE38,145 E | | 6/2003 | Lynn |
| 6,575,960 B2 | | 6/2003 | Becker et al. |
| 6,582,390 B1 | | 6/2003 | Sanderson |
| 6,602,240 B2 | | 8/2003 | Hermann et al. |
| 6,623,460 B1 | * | 9/2003 | Heck .............................. 604/256 |
| 6,634,364 B2 | | 10/2003 | Westlund et al. |
| 6,645,178 B1 | | 11/2003 | Junker et al. |
| 6,663,599 B2 | | 12/2003 | Osbourne et al. |
| 6,695,820 B1 | | 2/2004 | Armstrong et al. |
| 6,712,789 B1 | | 3/2004 | Lange et al. |
| 6,712,791 B2 | | 3/2004 | Lui et al. |
| 6,723,073 B2 | | 4/2004 | Ley et al. |
| 6,966,896 B2 | | 11/2005 | Kurth et al. |
| 6,969,381 B2 | | 11/2005 | Voorhees |
| 7,101,353 B2 | | 9/2006 | Lui et al. |
| 7,192,433 B2 | | 3/2007 | Osypka et al. |
| 2001/0020153 A1 | | 9/2001 | Howell |
| 2002/0072712 A1 | | 6/2002 | Nool et al. |
| 2003/0216771 A1 | | 11/2003 | Osypka et al. |
| 2004/0097903 A1 | * | 5/2004 | Raulerson ..................... 604/523 |
| 2004/0127855 A1 | | 7/2004 | Core |
| 2004/0153021 A1 | | 8/2004 | Osborne et al. |
| 2004/0172008 A1 | | 9/2004 | Layer |
| 2004/0260243 A1 | | 12/2004 | Rickerd |
| 2004/0267202 A1 | | 12/2004 | Potter |
| 2005/0020981 A1 | | 1/2005 | Kurth |
| 2005/0033239 A1 | | 2/2005 | Argentine |
| 2005/0085789 A1 | * | 4/2005 | Khan et al. ..................... 604/500 |
| 2005/0228346 A1 | | 10/2005 | Goode et al. |
| 2006/0145116 A1 | * | 7/2006 | Rickerd et al. ................ 251/331 |
| 2006/0167417 A1 | | 7/2006 | Kratz et al. |

FOREIGN PATENT DOCUMENTS

| | | | |
|---|---|---|---|
| EP | 1 002 553 | | 10/2003 |
| WO | 9934849 | | 7/1999 |
| WO | WO 9934849 A1 | * | 7/1999 |
| WO | 0117587 | | 3/2001 |
| WO | 03039625 | | 5/2003 |
| WO | 2004112865 | | 12/2004 |

\* cited by examiner

BREAK-AWAY HEMOSTASIS HUB

CROSS REFERENCE TO RELATED APPLICATIONS

The present application claims priority under 35 U.S.C §119 to U.S. Provisional Application No. 60/864,895 filed Nov. 8, 2006, entitled "Break-Away Hemostasis Hub," which is incorporated herein by reference.

TECHNICAL FIELD

The present invention relates generally to the field of medical instruments, and more particularly to catheter hemostasis hubs and valves for use in catheterization and related procedures.

BACKGROUND

Various medical procedures require the introduction of one or more medical instruments into arteries or veins so that the medical instruments may be advanced to a body location requiring diagnosis or treatment. For example, a guide catheter may be advanced through the patient's vasculature to a desired treatment location, such as the right atrium of the patient's heart, for delivery of a cardiac lead. A hub (e.g., a luer fitting) is typically coupled to the proximal end of the catheter to facilitate manipulation (e.g., rotation and translation) of the catheter by the clinician. Additionally, a hemostasis valve is further typically coupled to the hub and operates to control or inhibit the flow of blood out of the guide catheter lumen. A medical electrical lead or other device (e.g., a guide wire) may be inserted through the hemostasis valve, the hub, and the guide catheter lumen and into the patient's vasculature, with the hemostasis valve operating to inhibit blood flow around the lead.

There exists a continuing need for improved hemostasis valves and catheter hubs that can facilitate removal of the catheter from the patient's body while leaving the lead in place in the patient's body.

SUMMARY

The present invention, in one embodiment, is a hemostasis hub for use with a catheter including a lumen and a proximal end, the hemostasis hub comprising a housing including a proximal portion and a distal portion configured to be coupled to the proximal end of the catheter, a hemostasis seal in the proximal portion of the housing, and an actuator partially slidably disposed within the proximal portion of the housing. The housing is configured to be splittable or separable into first and second housing elements. The actuator includes a body portion, a dilator member extending distally from the body portion, and a lumen extending through the body portion and the dilator member. The actuator is further configured to assume a closed position in which the actuator lumen is fluidly isolated from the catheter lumen by the hemostasis seal, and an open position in which the dilator member extends through the hemostasis seal and the actuator lumen is in fluid communication with the catheter lumen.

In another embodiment, the present invention is a splittable or separable hemostasis hub for use in combination with a catheter having a proximal end and a lumen extending distally from the proximal end, the hemostasis hub comprising a splittable or separable housing having a proximal portion and a distal portion configured to be coupled to the proximal end of the catheter and defining an interior space, a hemostasis seal within the housing, and an actuator partially slidably disposed in the interior space. The actuator includes a dilator member configured to dilate the seal, and an actuator lumen extending through the dilator member.

In yet another embodiment, the present invention is a catheter and hemostasis hub assembly comprising an elongate catheter and a hemostasis hub. The catheter includes a proximal end and a lumen extending distally from the proximal end. The hemostasis hub is coupled to the proximal end of the catheter, and includes a housing, a resilient seal member, and an actuator. The housing defines an interior space in fluid communication with the catheter lumen, and includes a proximal portion and a distal portion coupled to the proximal end of the catheter. The housing us includes first and second housing elements. The seal member is located within the housing and is configured to hemostatically isolate the catheter lumen from the open proximal end of the housing. The actuator includes mating first and second actuator elements partially slidably disposed within the housing configured to dilate the seal for introducing an elongate medical device or instrument into the catheter lumen. The hub is further configured to be splittable into a first hub subassembly including the first housing element and the first actuator element, and a second hub subassembly including the second housing element and the second actuator element.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
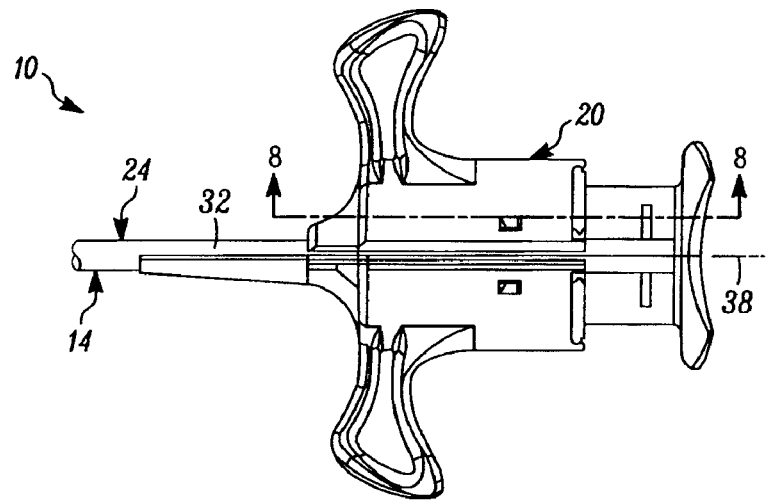
FIGS. 1A and 1B are side views of a portion of a catheter assembly including a catheter coupled to a splittable hemostasis hub according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1B:
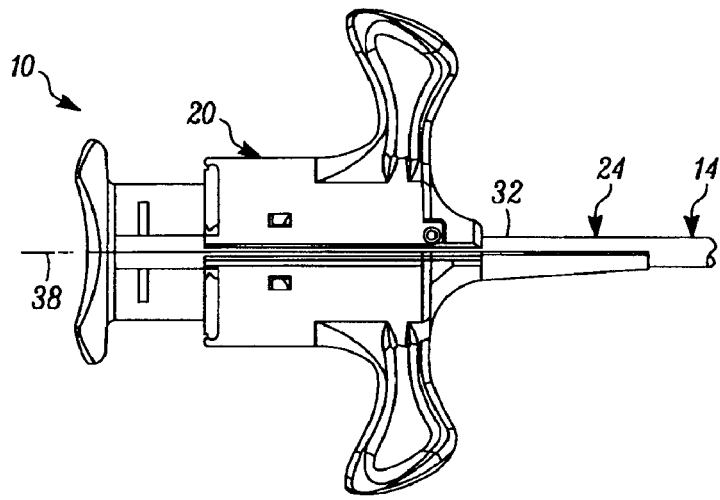

FIGS. 1A and 1B are side views of a portion of a catheter assembly 10 including a guide catheter 14 coupled to a hemostasis hub 20 according to one embodiment of the present invention. The catheter assembly 10 may be used in any medical procedure requiring catheterization. The catheter 14 has a body 24 including a proximal end portion 32, and can be any catheter, whether now known or later developed, for use in delivery and/or deployment of implantable medical devices (e.g., medical electrical leads, stents, and implantable sensors) or other catheterization procedures (e.g., drug delivery, mapping, and ablation). As will be appreciated, the catheter 14 includes at least one internal lumen through which the implantable medical device (e.g., lead), other therapeutic materials, e.g., drugs, biologicals, and the like, can be introduced into the patient's vasculature. In one embodiment, the catheter 14 is of a type configured for accessing and cannulating the coronary sinus and branch vessels thereof for delivery of cardiac leads for left ventricular pacing. In one embodiment, a lead can extend through the catheter 14 and the hub 20 for delivery to and fixation within the patient's heart or coronary venous system. In another embodiment, the catheter 14 may be an outer guide catheter, and a smaller diameter inner catheter may be extended through the hub 20 and the catheter 14. In the latter embodiment, the inner catheter may itself include a hub, which may be similar or identical to the hub 20, coupled to its proximal end.

As will be explained in greater detail below, the hub 20 includes a resilient seal element adapted to inhibit the flow of blood or other bodily fluids out of the catheter assembly 10 and to maintain a substantially positive fluid seal around a medical electrical lead (or other device such as, for example, an inner catheter, or guidewire) extending through the hub 20. Additionally, the hub 20 includes mechanisms for dilating the seal so as to permit a lead, catheter, or other device to be advanced through the hub 20 without excessive resistance. Still additionally, the hub 20 is splittable or breakable along a break line 38 into two generally symmetrical sub-assemblies, as will also be explained in greater detail below.

In the illustrated embodiment, the hub 20 is shown coupled to the catheter 14 to form the catheter assembly 10. It is emphasized, however, that in other embodiments, the hub 20 may be used in conjunction with other medical devices or instruments. For example, in one embodiment, an introducer sheath may be coupled at its proximal end to the hub 20, which may provide substantially the same or identical functionality as described herein in connection with the catheter assembly 10. In some embodiments, such introducer sheaths may be slittable, splittable or peel-away introducer sheaths as are known. Those skilled in the art will recognize other or additional applications of the hub 20 based on the foregoing.

Figure 2:
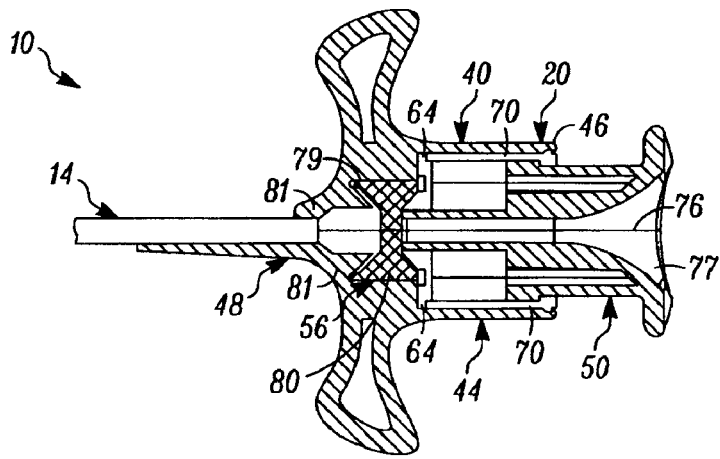
FIG. 2 is a cross-sectional elevation view of the hub shown in FIG. 1A.

FIG. 2 is a cross-sectional elevation view of the catheter assembly 10 shown in FIG. 1A. As shown in FIG. 2, the hub 20 includes a housing 40 having a proximal portion 44 with an open proximal end 46, a distal portion 48, an actuator 50, a seal 56, a pair of spring retainer elements 64, and a pair of actuator retainer members 70. The actuator 50 is partially slidably disposed within the proximal portion 44 of the housing 40, and includes a lumen 76 that is generally axially aligned with the lumen of the catheter 14. As shown, the lumen 76 includes a generally conical proximal region 77. The lumen 76 is sized to accommodate whatever elongate medical device (e.g., another catheter, a lead, a guidewire, and the like) the clinician desires to insert through the hub 20 and the catheter 14. As further shown, the spring retainer elements 64 are also disposed within the proximal portion 44 of the housing 40.

The seal 56 is configured to maintain hemostasis when the catheter is partially located in the patient's vascular system, and also to maintain a substantially positive fluid seal around a medical device that is passed through the seal 56 and hub 20 generally. In one embodiment, the seal 56 is constructed of two mating seal elements 79, 80 separable along a line generally aligned with the break line 38 of the hub 20. In one embodiment, the seal 56 may be a single-piece construction that is readily splittable, e.g., along a line of separation generally corresponding and/or aligned with the break line 38 of the hub 20. Alternatively, the seal 56 may be a one-piece construction that is cut away after splitting the hub 20. In various embodiments, the seal 56 may be any of the seals disclosed in co-pending and commonly assigned U.S. patent application Ser. No. 11/257,207, the contents of which are incorporated herein by reference for all purposes. The spring retainer elements 64 are positioned proximal to the seal 56 and, in some embodiments, operate to support the seal 56 under conditions of use.

As will further be explained in detail below, the actuator retainer members 70 are configured to cooperate with structures in the housing 40 so as to retain the actuator 50, and in turn, the seal 56 and the spring retainer elements 64, within the housing 40. Additionally, the actuator 50 is operable by a clinician to dilate the seal 56 and to provide a channel for relatively unimpeded introduction of the lead, inner catheter, guidewire, or other device, into and through the lumen of the catheter 14. In the illustrated embodiment, the hub 20 further includes distal seal support elements 81 which operate to support the seal against axial deformation (e.g., such as caused by dilation of the seal 56 as it is dilated by the actuator 50 or as an elongate body such as a lead or inner catheter is inserted), and to retain the seal elements 79, 80 within the respective hub sub-assemblies after the hub 20 is split.

Figure 3A:
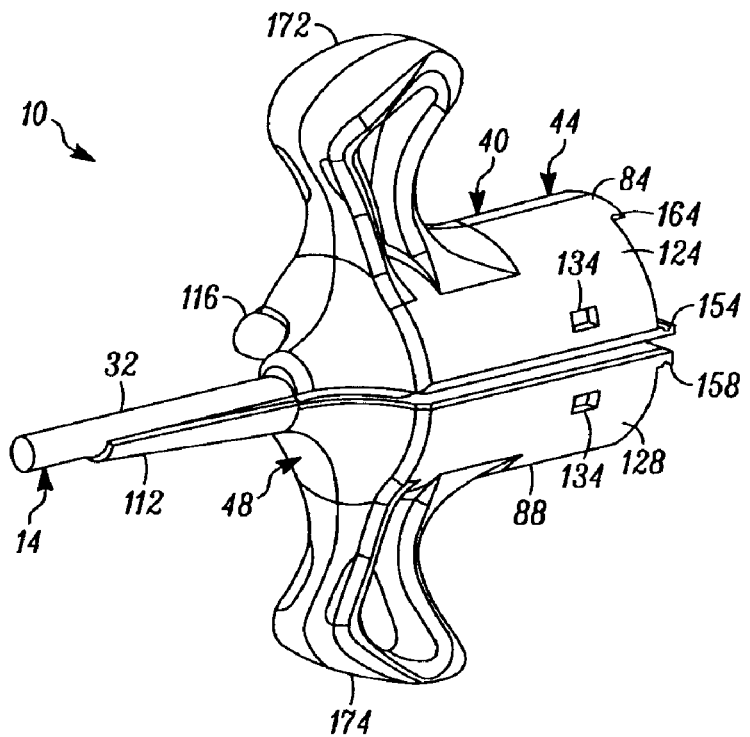
FIGS. 3A through 3D illustrate a housing of the hub of FIGS. 1A and 1B according to one embodiment of the present invention.
Figure 3B:
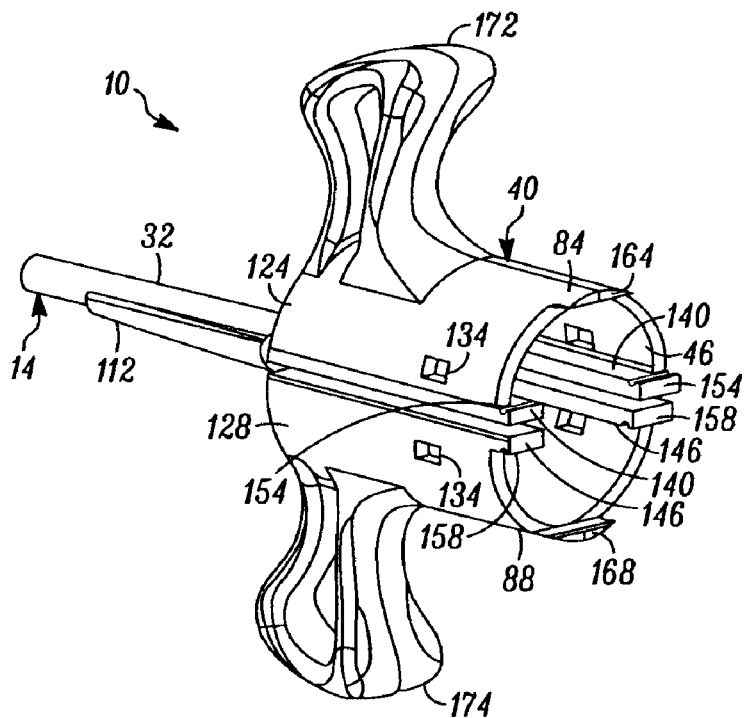
Figure 3C:
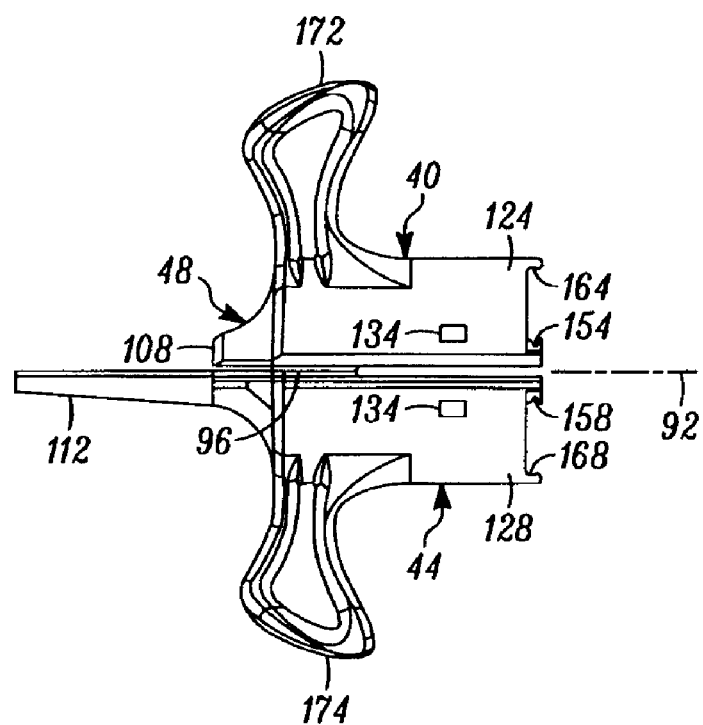
Figure 3D:
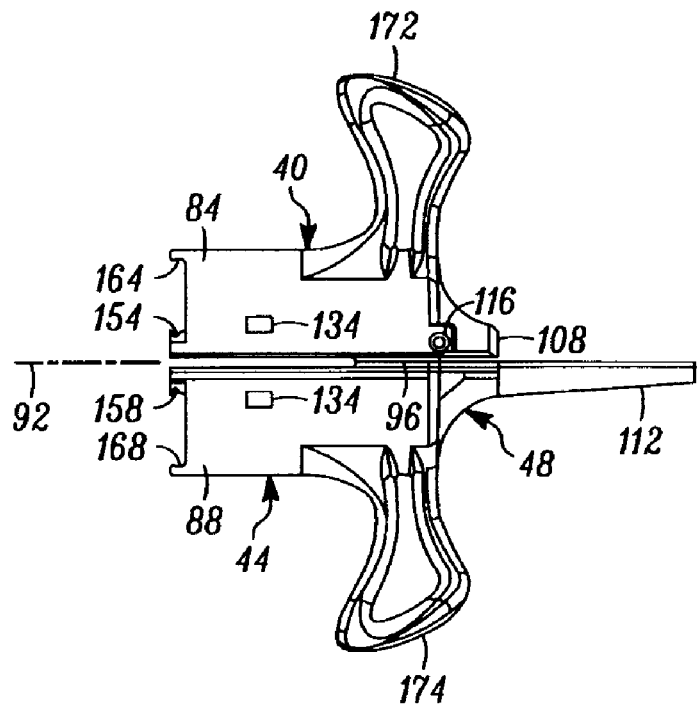
Figure 4A:
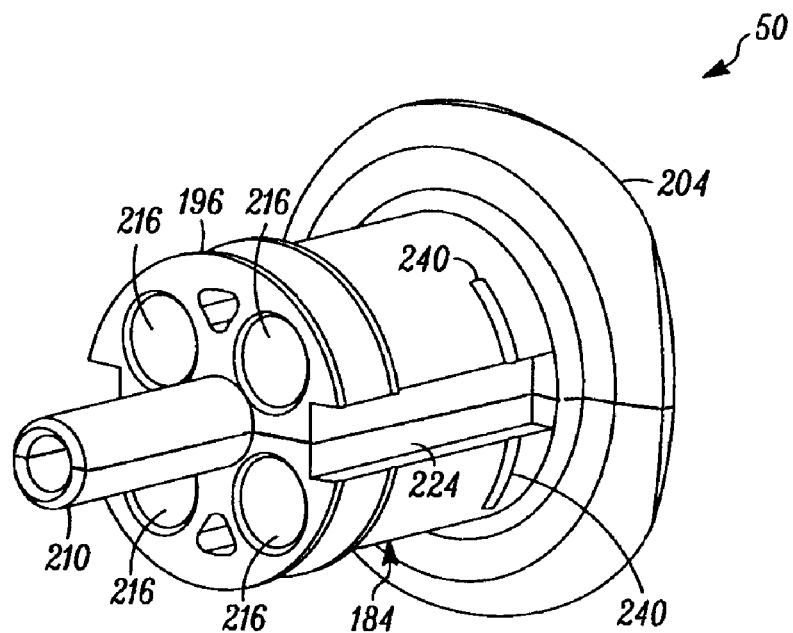
FIGS. 4A through 4D illustrate an actuator of the hub of FIGS. 1A and 1B according to one embodiment of the present invention.
Figure 4B:
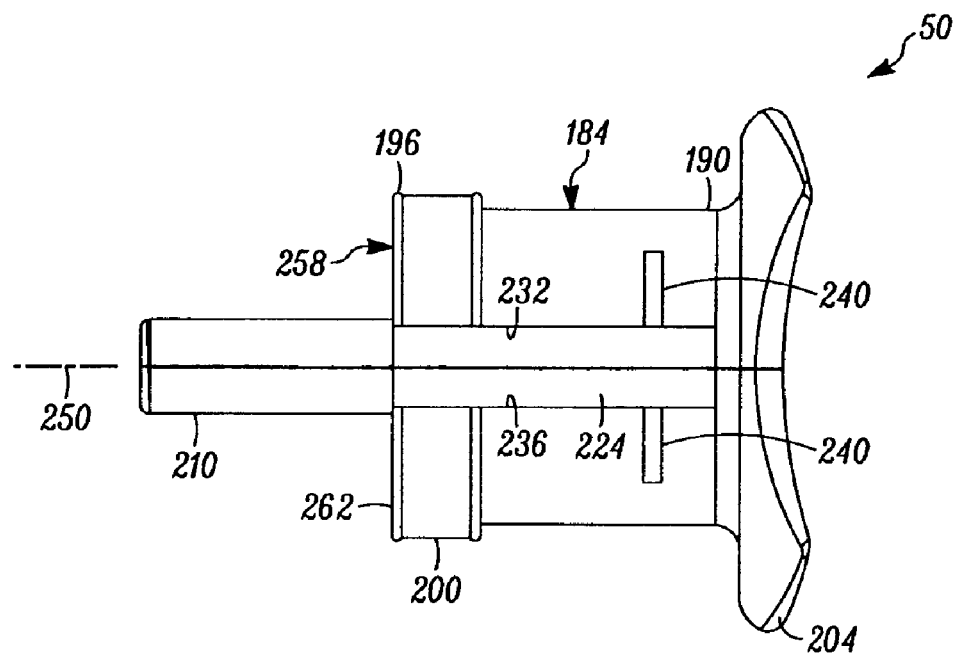
Figure 4C:
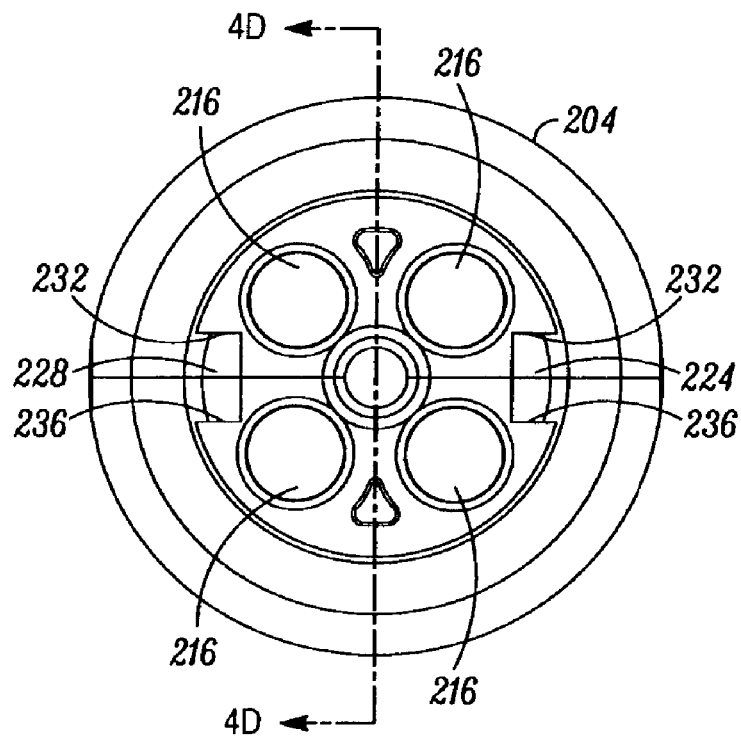
Figure 4D:
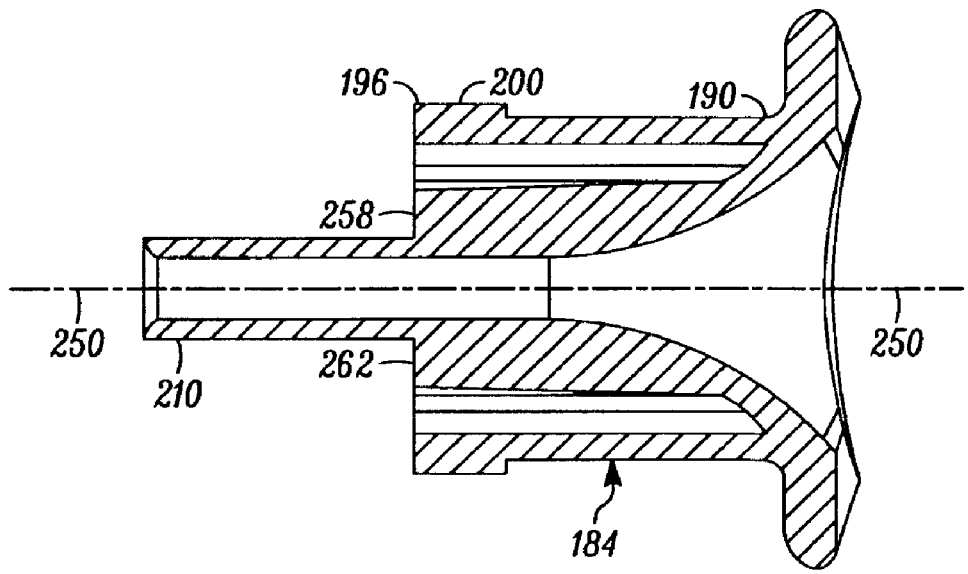

FIGS. 3A and 3B are perspective views of the housing 40 with the proximal end portion 32 of the catheter 14 coupled thereto, and FIGS. 3C and 3D are side views of the hub 20, according to one embodiment of the present invention. As shown, in the illustrated embodiment, the housing 40 includes first and second housing elements 84, 88 joined at a break line 92 corresponding to the general break line 38 of the hub 20. The housing 40 further includes joints 96 in the break line 92 extending along a portion of the proximal portion 44 and connecting the first and second housing elements 84, 88. In other embodiments, the joints 96 may extend along the entire proximal portion 44. In other embodiments, the first and second housing elements 84, 88 may be joined in the distal portion 48.

In various embodiments, the joints 96 may be weakened areas configured to facilitate splitting the housing 40 into two substantially symmetrical sub-assemblies, each contained within one of the first and second housing elements 84, 88, as will be explained in greater detail below. In one embodiment, the housing 40 may be a single component (i.e., in which the housing elements 84, 88 are integrally formed) and the joints 96 are weakened or relatively thin regions along the break line 92. In one embodiment, the joints 96 are have substantially uniform configurations along their lengths. In other embodiments, portions of the respective joints may be stronger than other portions. In one exemplary embodiment, the proximal end portions of the joints 96 may be configured to be stronger than the more distal portions of the joints 96, e.g., by forming the more proximal portions to be thicker than the more distal portions, so as to inhibit undesired splitting of the housing 40, and thus the hub 20, in the absence of an external force applied by the clinician. In one embodiment, the housing 40 may be made from separate housing elements 84, 88 mechanically joined, or connected by adhesive joints or other joining techniques as may be known in the art, such that the housing elements 84, 88 are separable by the clinician.

As shown, the distal portion 48 of the housing 40 includes a distal end 108 adapted to receive the catheter proximal end portion 32, which may be fixedly or alternatively, releasably attached to the distal portion 48. As further shown, the distal portion 48 includes a ferrule 112 on the second housing element 88 which is configured to support and provide strain relief as well as a platform for attaching the catheter distal end portion 32 to the housing element 88. In one embodiment, the catheter proximal end portion 32 is fixedly or releasably attached to the ferrule 112. The distal portion 48 further includes a flush port 116 in fluid communication with the interior space within the distal portion 48 and in turn, the catheter lumen (see FIG. 2). The flush port 116 can be used for a variety of functions as are known in the art, such as, for example, drug delivery, flushing the catheter 14 to remove air and other gases prior to insertion into the patient's venous system, and the like.

As further shown, the proximal portion 44 of the housing 40 is generally cylindrical, and the first and second housing elements 84, 88 are generally symmetrical in the proximal portion 44 and include, respectively, semi-cylindrical wall members 124, 128. Additionally, each of the housing elements 84, 88 includes a pair of circumferentially spaced apertures 134 through the wall members 124, 128 in the respective proximal portions.

As can be seen in at least FIG. 3B, the housing element 84 includes internal ledges 140 extending longitudinally from the proximal end 46. Similarly, the housing element 88 includes internal ledges 146 extending longitudinally from the proximal end 46. The ledges 140, 146 include, respectively, slotted proximal end portions 154, 158. Additionally, the housing elements 84, 88 further include slotted segments 164, 168 extending circumferentially along portions of their respective wall members 124, 128 adjacent the proximal end 46. As will be explained in more detail below, the apertures 134 and the aforementioned slotted portions of the housing elements 84, 88 are positioned and configured to engage portions of the actuator retainer members 70 so as to retain the actuator 50 and the spring retainer elements 64 within the housing 40. In some embodiments, the slotted end portions 154, 158 or the slotted segments 164, 168 of the housing elements 84, 88, respectively, may be omitted, and other structures may be included to retain the actuator 50 and the spring retainer elements 64 in the housing 40.

In the illustrated embodiment, the housing 40 includes handle members 172, 174 extending from the housing 40 and disposed approximately 180 degrees apart in the proximal portion 44. The handle members 172, 174 are adapted to be gripped by a clinician (i.e., by the pointer and forefingers) for manipulation of the catheter assembly 10. In other embodiments, the housing 40 may include other structures to facilitate manipulation by the clinician. Alternatively, in some embodiments, one or both of the handle members 172, 174 (or comparable structures) may be omitted.

FIGS. 4A through 4D illustrate the actuator 50 according to one embodiment of the present invention. As shown, the actuator 50 includes a body portion 184 having a proximal end 190 and a distal end 196, a distal rim 200, a flange 204 on the proximal end 190, and a dilator member 210 extending distally from the distal end 196. As further shown, the actuator 50 further includes a plurality of generally cylindrical recessed channels 216 extending proximally from the distal end 196 of the body 184, a pair of longitudinal slots 224, 228 defining shoulders 232, 236 extending proximally from the distal end 196, and a plurality of ribs 240 extending partially circumferentially around the body portion 184. The body portion 184 is dimensioned such that it can be slidably disposed within the proximal portion 44 of the housing 40 through the open proximal end 46. The slots 224, 228 are configured such that the shoulders 232, 236 can slidably contact the ledges 140, 146 of the housing 40, so as to slidably support the actuator 50 within the housing 40. In the illustrated embodiment, the actuator 50 is configured to be splittable or separable along a longitudinal actuator break line 250 into mating first and second actuator elements 258, 262. In various embodiments, the actuator 50 is configured such that the break line 250 is generally aligned, in the assembled hub 20, with the break line 92 of the housing 40.

FIGS. 5A through 5D illustrate one of the spring retainer elements 64 according to one embodiment of the present invention. As shown, the spring retainer elements 64 each include a generally semi-circular disc portion 270 having a proximal face 276 and a distal face 282. The disc portion 270 further includes a pair of generally tubular spring retainer members 288 extending proximally from the proximal face 276. Each of the spring retainer members 288 is sized to receive a helical spring and also to be slidably received within one of the recessed channels 216 of the actuator body portion 184. The disc portion 270 includes a semi-annular flange member 294 and a seal support portion 298 extending from the distal face 282. As shown, the flange member 294 extends radially beyond the disc portion 270, and is radially spaced from the seal support portion 298 so as to form a seal retaining slot 304. As further shown, in the illustrated embodiment, the peripheral portions of the disc portions 270 and the flange members 294 form shoulders 310.

In the assembled hub 20, the seal support portions 298 of the pair of spring retainer elements 64 form a generally conical bearing surface which advantageously mates with the generally conical entrance area of the seal disclosed in co-pending and commonly assigned U.S. patent application Ser. No. 11/257,207 incorporated by reference above. The seal support portions 298 thus advantageously support the seal 56 and inhibit excessive seal deformation during operation. The seal retaining slot 304 is sized to receive an annular rim of the seal 56 for maintaining the resilient seal 56 in position within the hub 20.

Figure 5A:
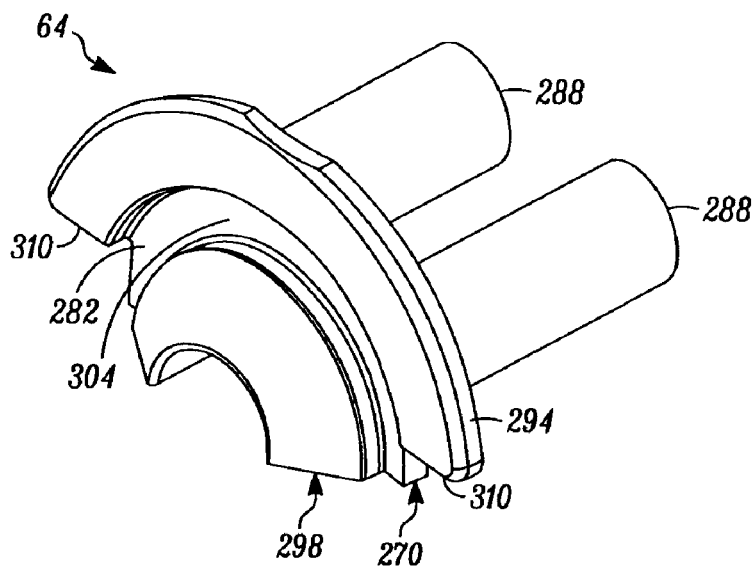
FIGS. 5A through 5F illustrate a spring retainer elements for use in the hub of FIGS. 1A and 1B according to one embodiment of the present invention.
Figure 5B:
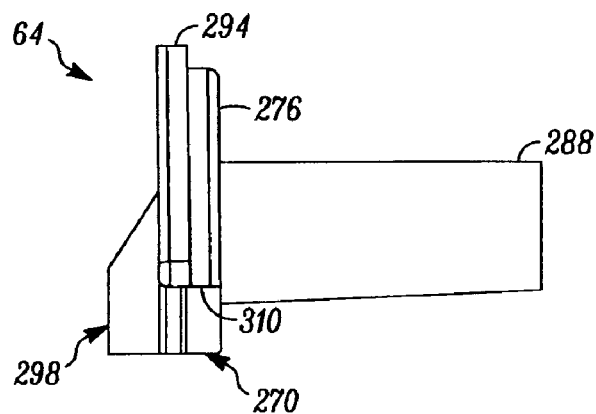
Figure 5C:
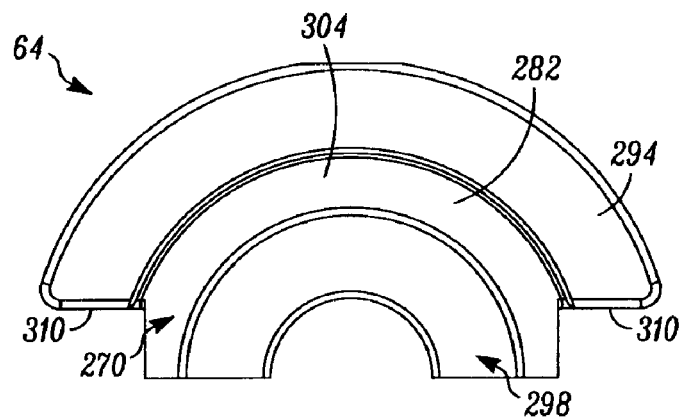
Figure 5D:
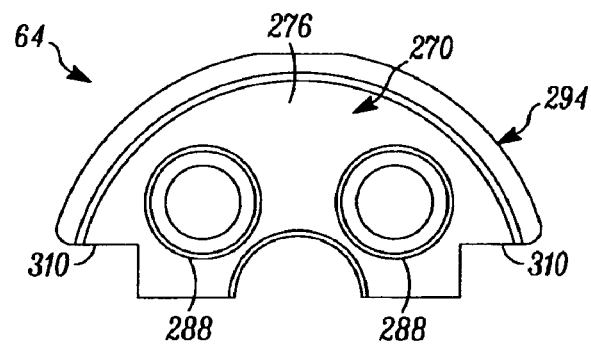
Figure 5E:
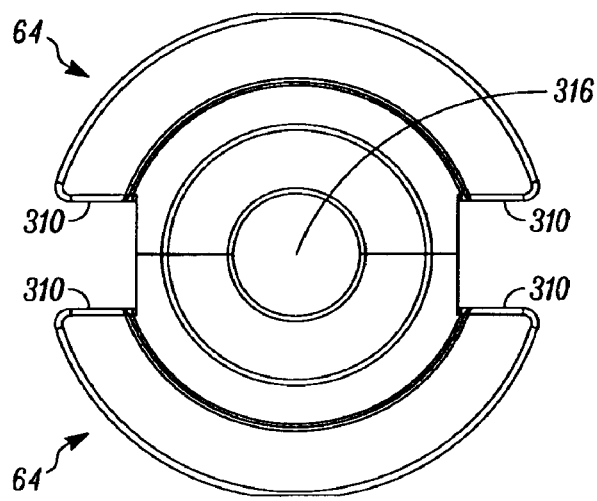
Figure 5F:
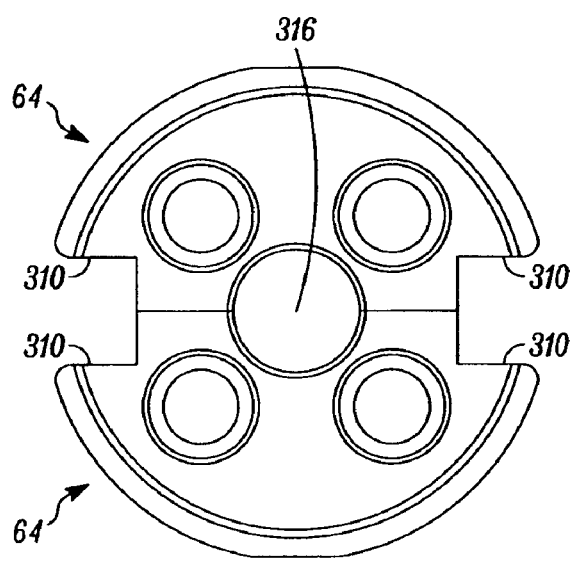

FIGS. 5E and 5F are distal and proximal end views, respectively, of the pair of spring retainer elements 64 mated together as in the assembled hub 20. As shown, the pair of spring retainer elements 64 mate to form an aperture 316 sized to receive the dilator member 210 of the actuator 50 (see, e.g., FIGS. 4A-4D). Additionally, the shoulders 310 are configured to bear upon and be restrained from rotational movement by the ledges 140, 146 of the housing proximal portion 44 (see, e.g., FIG. 3B).

Figure 6A:
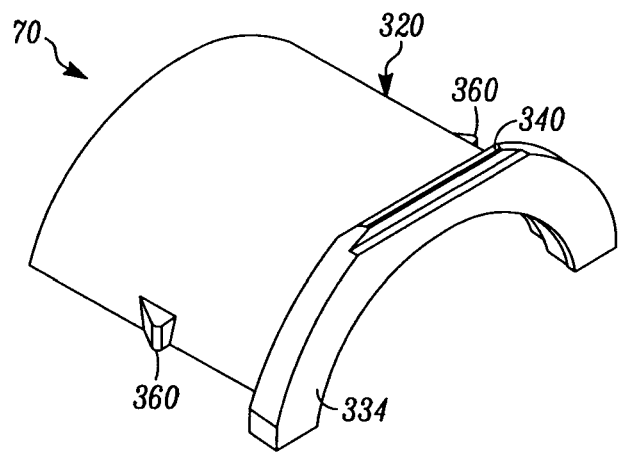
FIGS. 6A through 6D illustrate an actuator retainer member for use in the hub of FIGS. 1A and 1B according to one embodiment of the present invention.
Figure 6B:
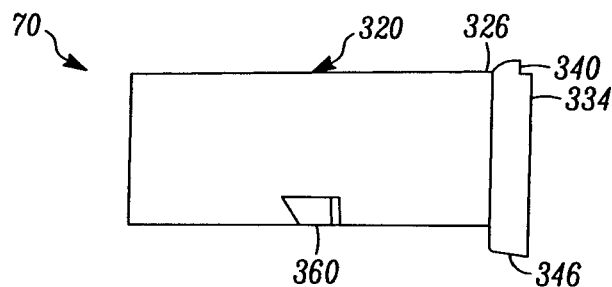
Figure 6C:
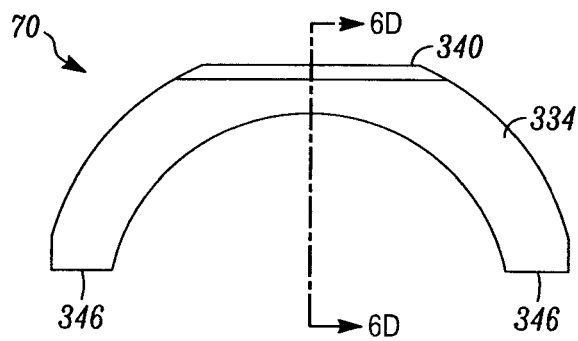
Figure 6D:
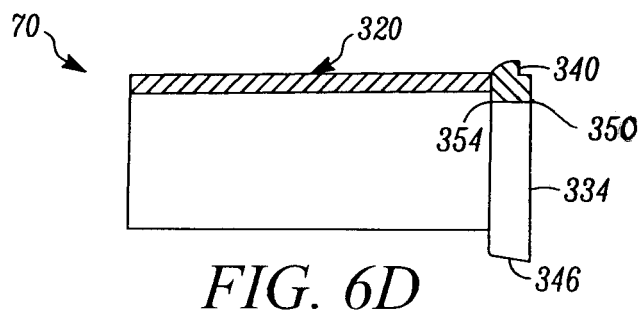

FIGS. 6A through 6D illustrate one of the actuator retainer members 70 according to one embodiment of the present invention. As shown in FIGS. 6A to 6C, the actuator retainer members 70 each include a generally semi-cylindrical sleeve portion 320 having a proximal end 326, and a flange 334 on the proximal end 326. The flange 334 includes a primary housing engagement lip 340, a pair of lateral housing engagement lips 346, an outer edge 350, and an inner edge 354. As further shown, the sleeve portion 320 includes a pair of detents 360 on its outer surface. In the assembled hub 20, the actuator retainer members 70 are configured to be inserted through the proximal end 46 of the housing 40, with the sleeve portion 320 adjacent the actuator body portion 184 (see, e.g., FIGS. 2 and 4A-4D). The primary housing engagement lips 340 are configured to fit within and engage the slotted segments 164, 168 of the respective housing elements 84, 88 (see FIGS. 3A-3D). Additionally, the lateral housing engagement lips 346 are configured to fit within and engage the slots in the slotted ledge proximal portions 154, 158, and the detents 360 are configured to extend through and engage the surfaces defining the apertures 134 in the housing wall members 124, 128 (see FIGS. 3A-3D).

Figure 7A:
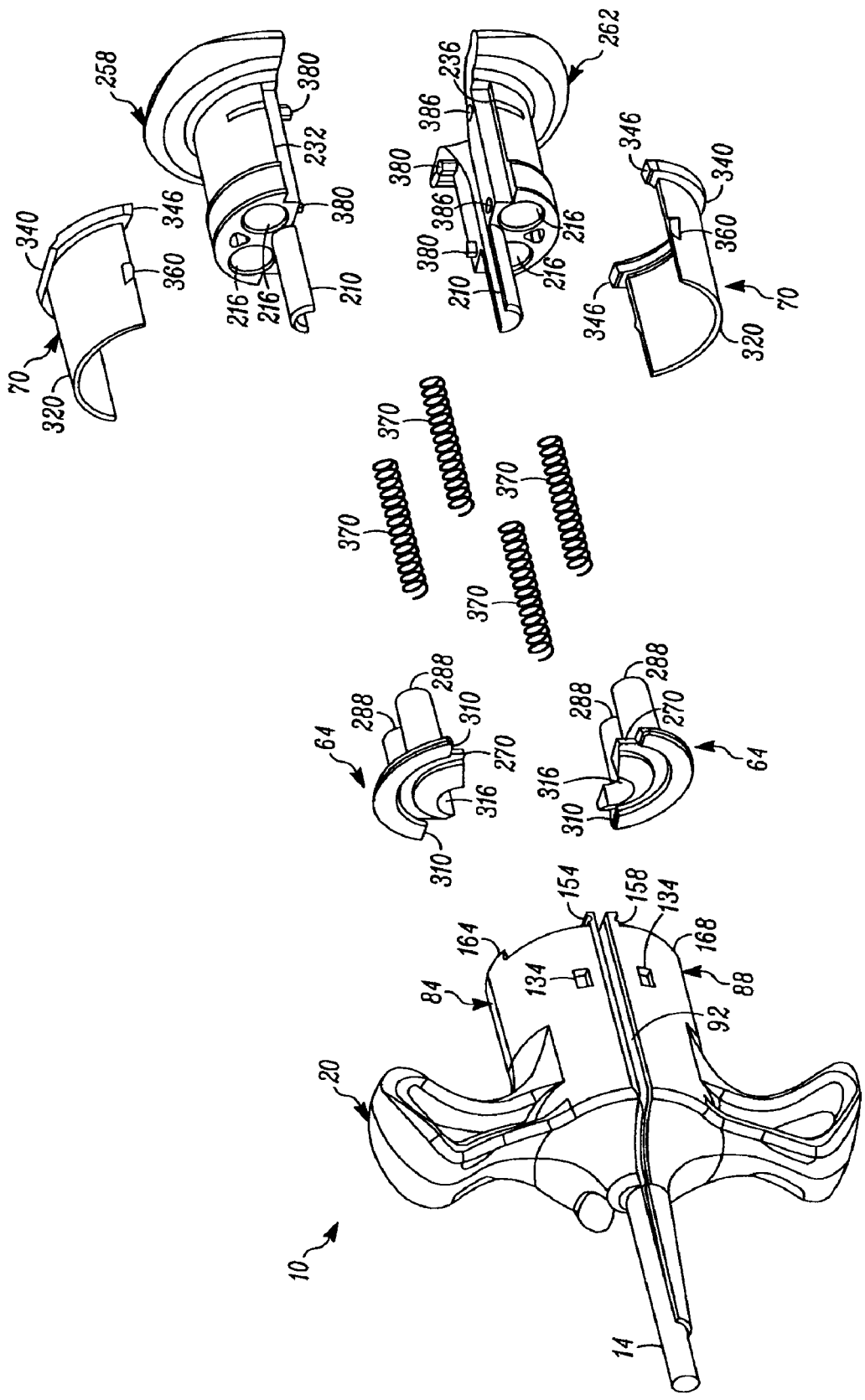
FIGS. 7A and 7B are distal and proximal perspective exploded views, respectively, of the hub of FIGS. 1A and 1B according to one embodiment of the present invention.
Figure 7B:
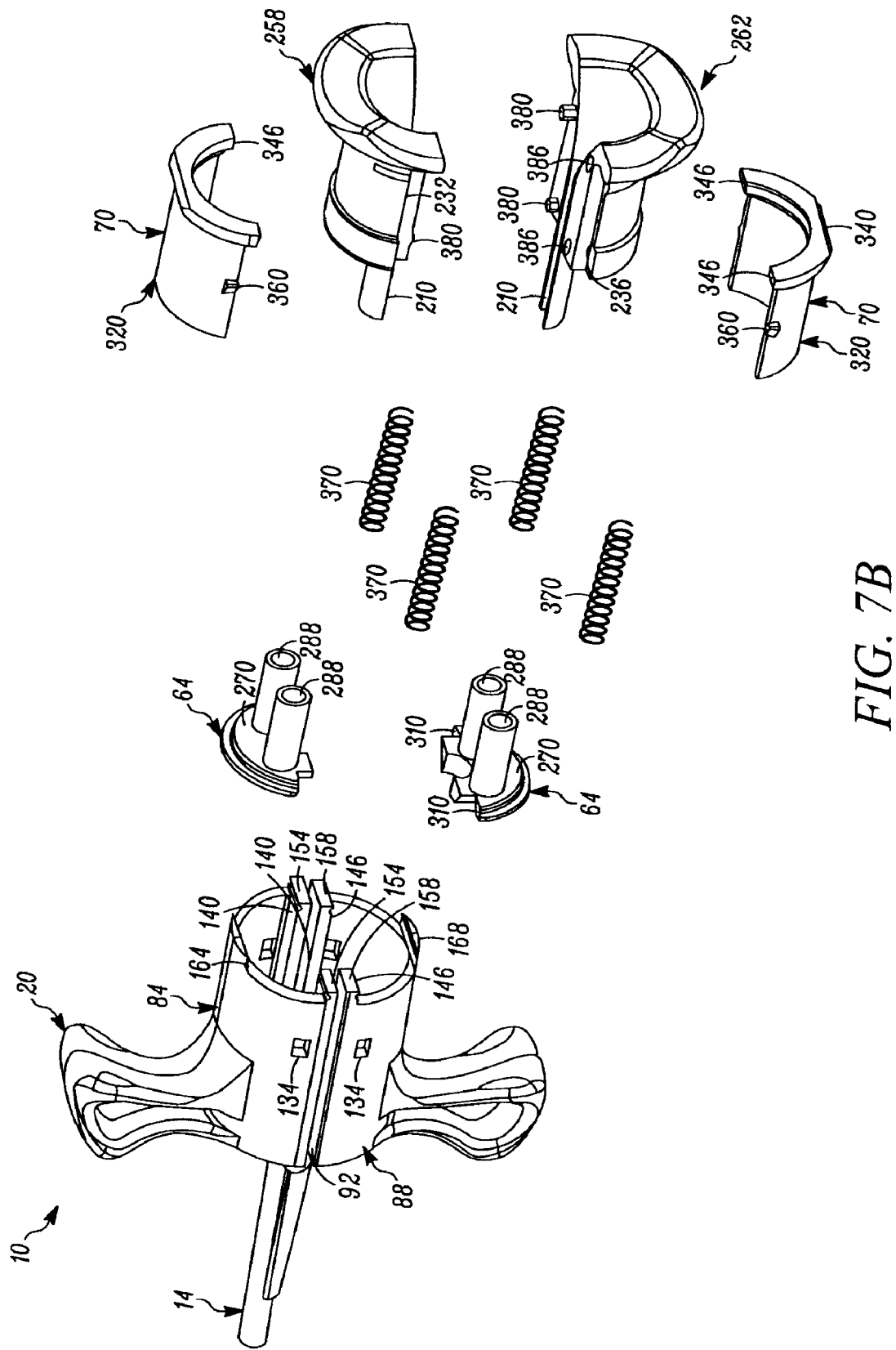
Figure 8:
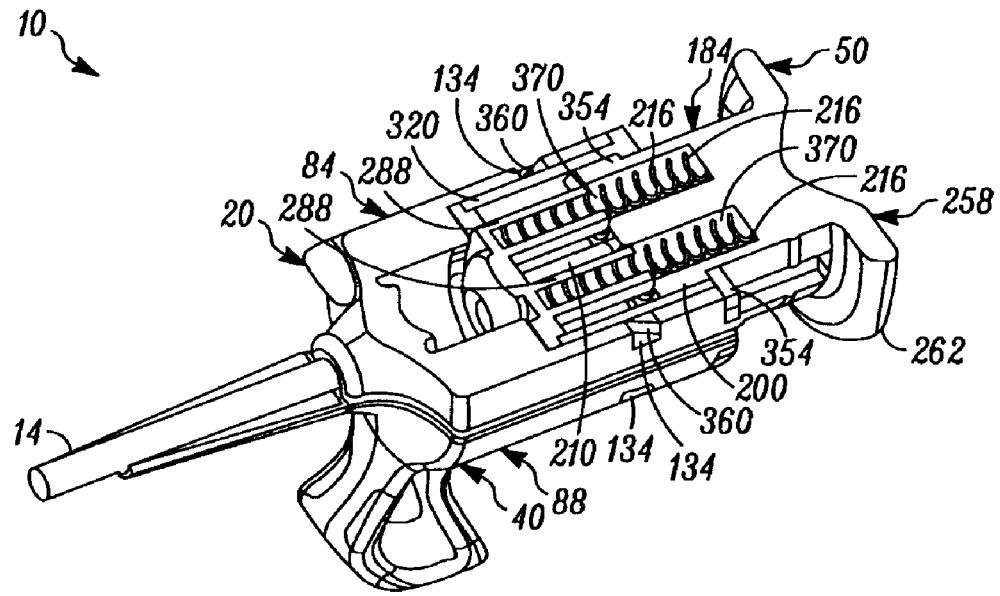
FIG. 8 is a cross-sectional perspective view of the assembled hub taken along the line 8-8 in FIG. 1A.

FIGS. 7A and 7B are distal and proximal perspective views, respectively, of the catheter assembly 10 each showing the hub 20 in an exploded view. FIG. 8 is a cross-sectional perspective view of the assembled hub 20 taken along the line 8-8 in FIG. 1A. In FIGS. 7A-7B and FIG. 8, the seal 56 has been omitted. The spring retainer elements 64 are inserted into the respective housing elements 84, 88 with the disc portions 270 arranged generally transverse to the longitudinal axis of the housing 40, the spring retainer members 288 extending toward the housing proximal end 46, and the aperture 316 formed by the mating spring retainer elements 64 (see FIGS. 5E and 5F) generally axially aligned with the catheter 14. When so inserted, the shoulders 310 of the spring retainer elements 64 bear upon the ledges 140, 146 of the housing elements 84, 88. A spring 370 is partially inserted into each of the spring retainer members 288. The springs 370 are dimensioned to extend proximally beyond the proximal ends of the spring retainer members 288.

The actuator elements 258, 262 can then be inserted into the housing elements 84, 88. When so inserted, the shoulders 232, 236 can slidably contact the ledges 140, 146, respectively, and the dilator member 210 can be partially inserted into or through the aperture 316 of the mating spring retainer elements 64. Additionally, each of the spring retainer members 288 can be partially slidably received within one of the channels 216 in the respective body portions of the actuator elements 258, 262. Thus, as can be seen in FIG. 8, in the assembled hub 20, each of the springs 370 is captured within one of the respective spring retainer members 288 and channels 216, such that each spring 370 bears upon the proximal face 276 of the respective spring retainer element 64 (see FIG. 5D) and also on the proximal end surface of the actuator body 184 within the respective channel 216. Accordingly, distal movement of the actuator 50 relative to the housing 40 compresses the springs 370, which operate to oppose such movement of the actuator 50.

In the illustrated embodiment, the actuator elements 258, 262 are separate components and each include projections 380 sized and positioned to be received in mating recesses 386 in the opposing actuator element so as to maintain the actuator 50 sub-assembly (See FIGS. 7A and 7B). In one embodiment, the projections 380 and the recesses 386 may be sized to create a nominal interference fit to releasably couple the actuator elements 258, 262 together. In some embodiments, the actuator elements 258, 262 may be coupled by an adhesive bond in lieu of or in addition to the mating projections 380 and recesses 386. It will be appreciated that the actuator elements 258, 262 may be pre-assembled into the actuator 50 prior to insertion of the actuator 50 into the housing 40. Additionally, in one embodiment, the actuator 50 is a single, splittable component having a weakened break line generally parallel to the break line 92 of the housing 40.

The actuator retainer members 70 can then be inserted into the housing elements 84, 88, with the sleeve portions 320 disposed between the actuator body portion 184 and the housing elements 84, 88. When the actuator retainer members 70 are fully inserted into the housing 40, the primary housing engagement lips 340 engage the slotted segments 164, 168, the lateral housing engagement lips 346 engage the slots in the slotted ledge proximal portions 154, 158, and the detents 360 extend through and engage the surfaces defining the apertures 134 in the housing wall members 124, 128. Additionally, the inner edges 354 of the actuator retainer members 70 operate, in one embodiment, to limit the travel of the actuator 50 in the proximal direction. That is, as can be seen in FIG. 8, the distal rim 200 of the actuator 50 contact the inner edges 354, such that further proximal movement of the actuator would require ejecting the actuator retainer members 70 from the housing 40. Accordingly, the actuator retainer members 70 operate to retain the actuator retainer elements 64, the springs 370, and the actuator elements 258, 262 within their respective housing elements 84, 88.

Various other embodiments of the present invention may include alternative or additional structures for retaining the actuator 50, the spring retainer elements 64, and the springs 370 within the respective housing elements 84, 88. For example, in some embodiments, the wall members 124, 128 of the housing elements 84, 88 may include detents adapted to engage apertures in the actuator retainer members 70 to retain the latter, and in turn, the other hub components, within the respective housing elements 84, 88. In some embodiments, the actuator retainer members 70 may include slots adapted to receive lips or other projections on the housing elements 84, 88. Additionally, as discussed above, in some embodiments, the slotted proximal end portions 154, 158 or the slotted segments 164, 168 of the housing elements 84, 88, respectively, may be omitted. In short, any structures capable of retaining the actuator retainer members 70, and in turn, the actuator 50 and the spring retainer elements 64, within the housing elements 84, 88, may be incorporated into the hub 20.

Figure 9:
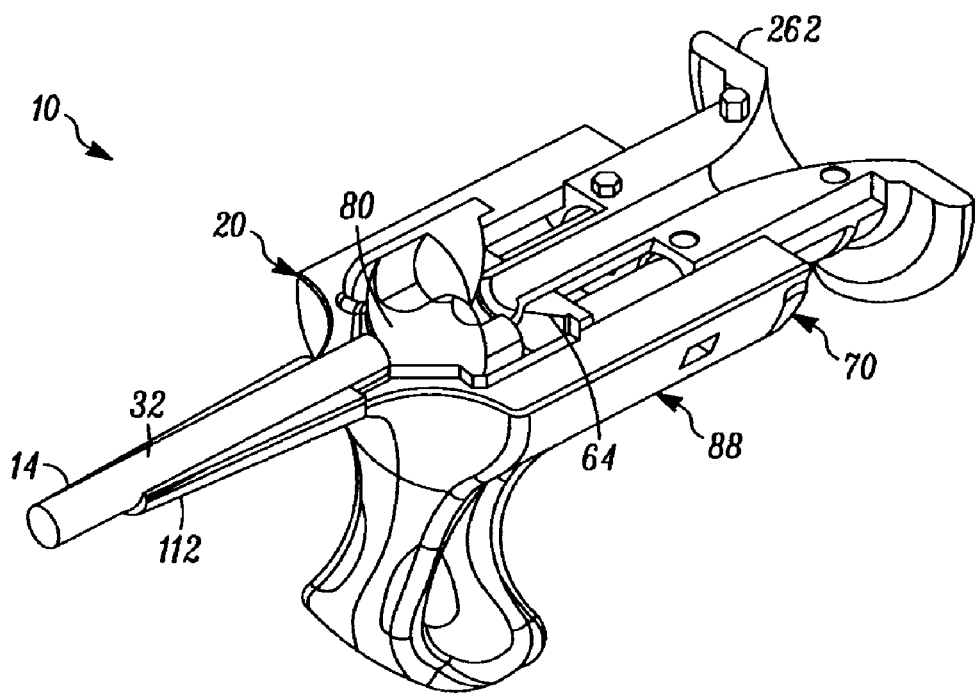
FIG. 9 is a perspective view of a hub subassembly after splitting the hub of FIGS. 1A and 1B along a break line.

FIG. 9 is a perspective view of the hub 20 subassembly contained within the housing element 88 after splitting the hub 20 along the break line 38. In the embodiment illustrated in FIG. 9, the actuator element 262, spring retainer element 64, actuator retainer member 70, and seal element 80 are retained within the housing element 88, thereby forming a hub subassembly. As further shown, a portion of the proximal end of the catheter 14 is exposed such that the catheter can be cut and retracted from the patient without disturbing its payload (e.g., a medical electrical lead). The ferrule 112 of the housing element 88 advantageously operates to support the catheter proximal end portion 32 and provide strain relief as the clinician cuts this portion of the catheter. In one embodiment, the hub 20 is used in conjunction with the cutters described in co-pending and commonly assigned U.S. Patent Application Publication 2005/0182435, and U.S. Provisional Patent Application 60/864,901 entitled "Universal Cutter for Guide Catheters," both of which are incorporated herein by reference. As will be appreciated, a second hub subassembly is formed by the actuator element 258, the spring retainer element 64, the actuator retainer member 70, and the seal element 79 associated with the housing element 84, and the two subassemblies are joined to form the completed hub 20. Formation of the subassemblies as shown advantageously allows the clinician improved control over the individual hub components after splitting or separating the hub 20.

Figure 10A:
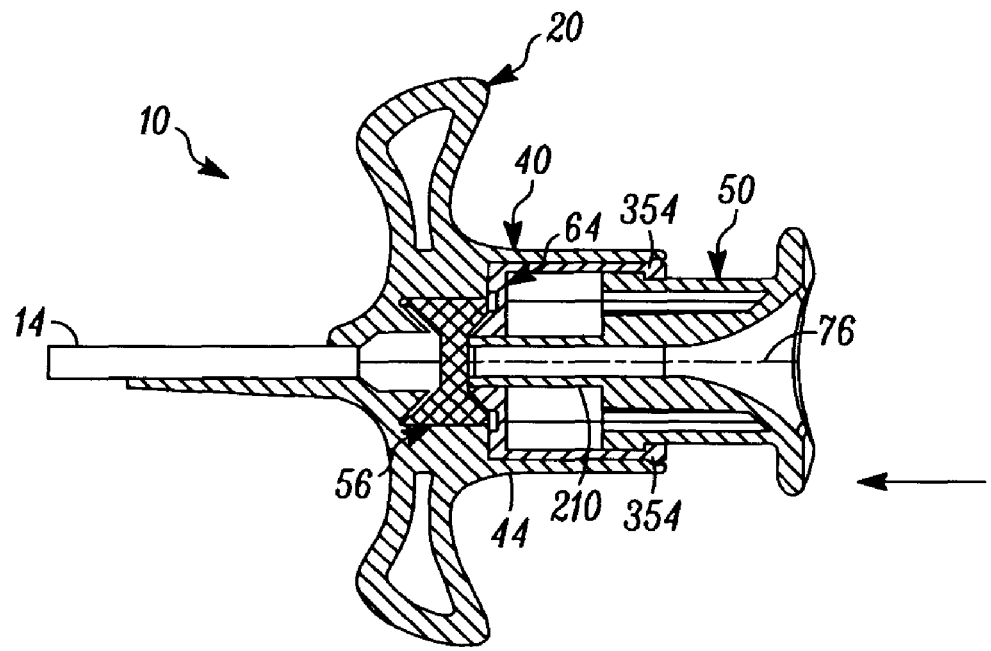
FIGS. 10A-10C are side cross-sectional elevation views of the hub of FIGS. 1A and 1B showing the actuator in closed and open positions, respectively.
Figure 10B:
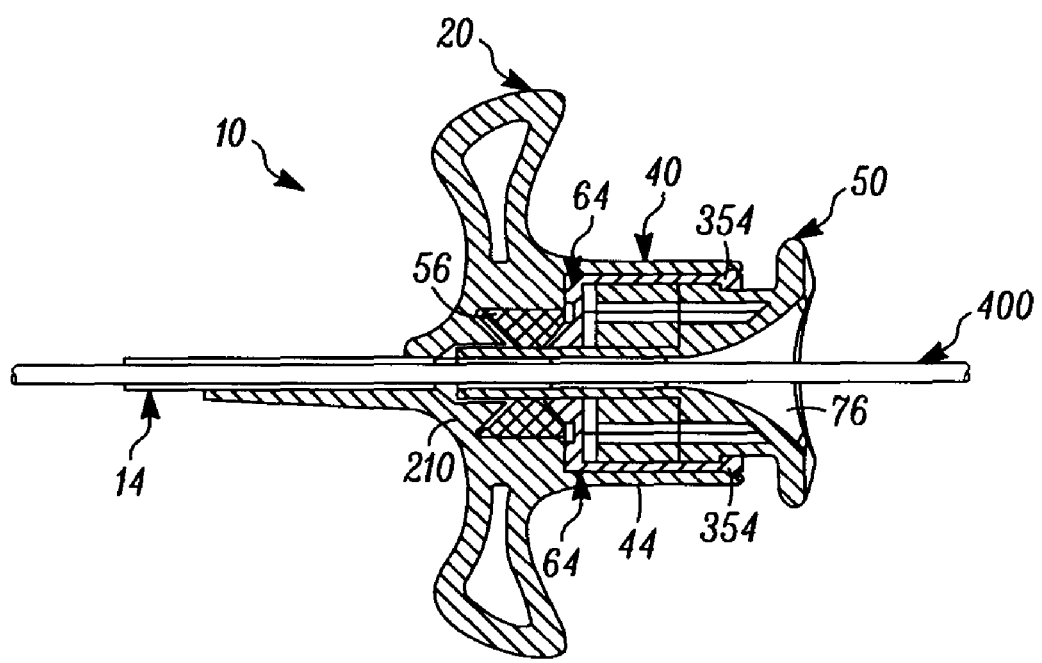
Figure 10C:
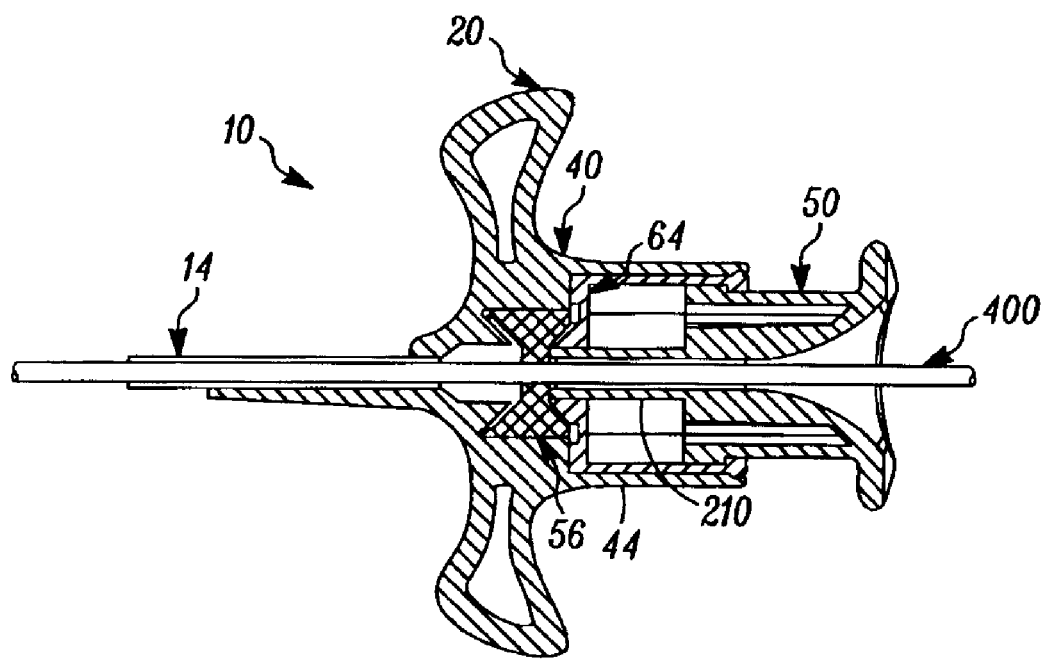

FIGS. 10A, 10B, and 10C are additional cross-sectional elevation views of the assembled hub 20. As can be seen by comparing FIG. 10A and FIG. 10B, the actuator 50 is slidably partially disposed within the housing 40 such that the actuator 50 is operable to assume a closed position in which the actuator 50 is retracted proximally as shown in FIG. 10A, and an open position in which the actuator 50 is fully advanced distally into the proximal portion 44 of the housing 40. As shown in FIG. 10A, in the closed position of the actuator 50, the dilator member 210 is proximal to the seal 56, such that the seal 56 hemostatically isolates the lumen of the catheter 14 from the actuator lumen 76 and the proximal portion of the housing 40. Additionally, as can be seen in FIG. 10B, in the open position of the actuator 50, at least a portion of the dilator member 210 extends through and dilates the seal 56, such that the actuator lumen 76 is in fluid communication with the lumen of the catheter 14. As shown, with the actuator 50 in the open position, a lead 400 or other elongate device (e.g., a catheter or guide wire) can be passed through the actuator lumen 76 and into the lumen of the catheter 14 without interference from the seal 56. As shown in FIG. 10C, the actuator 50 can then be returned to its closed position, thus allowing the seal 56 to close and seal around the lead or other device.

Additionally, as discussed above, the springs 370 disposed within the spring retainer members 288 and the recessed channels 216 in the actuator body portion 194 (see FIG. 8) operate to bias the actuator 50 to the closed position as shown in FIG. 10A. That is, distal movement of the actuator 50 relative to the spring retainer elements 64 (i.e., in causing the actuator 50 to move toward the open position of FIG. 10B) compresses the springs 370, which operate to resist such distal movement of the actuator 50. Thus, if the force pushing the actuator 50 into the housing 40 is released, the springs 370 will tend to cause the actuator 50 to move to the closed position and thus allow the seal 56 to maintain hemostasis. As discussed in greater detail below, however, where the actuator 50 is advanced sufficiently into the housing 40, the ribs 240 on the actuator body portion 184 (see FIG. 4A) are adapted to engage the inner edges 354 of the actuator retainer members 70 (see FIG. 6D), thus preventing the springs 370 from spontaneously forcing the actuator 50 to the closed position.

Figure 11:
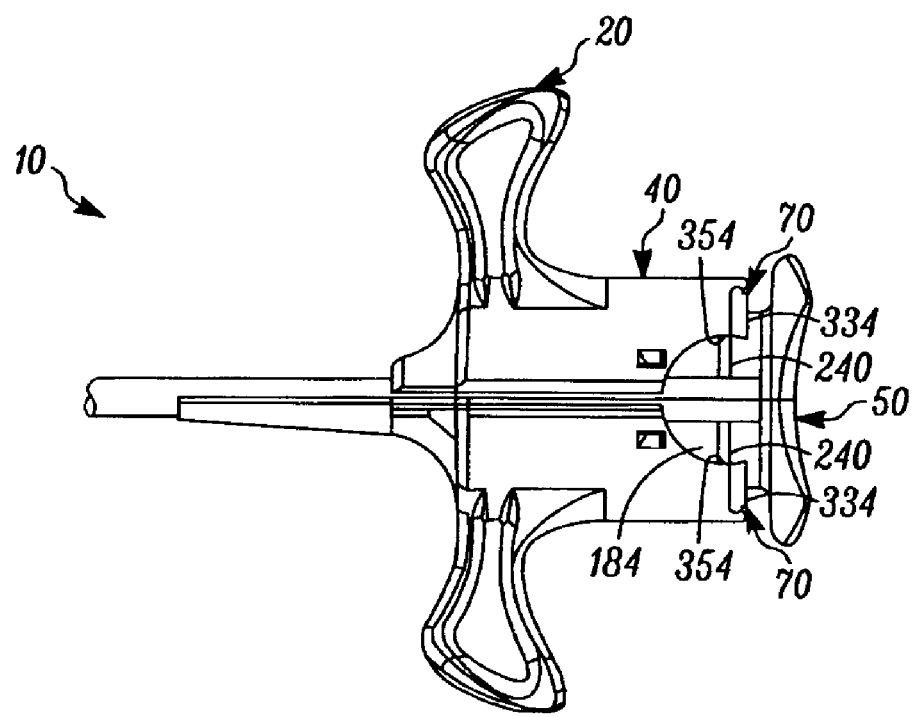
FIG. 11 is a side view of the hub of FIGS. 1A and 1B with a portion of the housing cut away.

FIG. 11 is a side view of the catheter assembly 10 showing the hub 20 with a portion of the housing 40 cut away to illustrate the position of the actuator ribs 240 relative to the inner edges 354 of the actuator retainer members 70 with the actuator 50 locked in the open position. As shown, the ribs 240 are positioned distal to the inner edges 354. Additionally, because the ribs 240 extend radially from the actuator body portion 184, the ribs 240 are configured to engage the inner edges 354, thus counteracting the forces imposed by the springs 370 (not shown in FIG. 11), which would otherwise tend to urge the actuator 50 proximally relative to the housing 40, i.e., to the closed position. In short, the interaction of the ribs 240 and the inner edges 354 of the actuator retainer members 70 effectively lock the actuator 50 in the open position. Furthermore, because the ribs 240 have a rounded shape, the actuator 50 can be advanced to the open position by the clinician without requiring excessive force to overcome the resistance caused by the engagement of the ribs 240 with the flanges 334 and inner edges 354. In one embodiment, the foregoing can be even further facilitated by configuring the distal faces of the ribs 240 to be sloped or ramped.

The sizes of the hub 20 and the catheter 14 may be dictated by the particular procedures and the needs of the clinician. In short, the hub 20 and catheter 14 can be sized to accommodate any desired clinical application, whether now known or later developed. In various embodiments, for example, the outside diameter of the catheter 14 may range in size from 4 French to 22 French. In other embodiments, smaller diameter or larger diameter catheters may be utilized. In one embodiment, the catheter 14 is a 6 French, 8 French, or 10 French guide catheter configured for accessing and cannulating the coronary sinus for left side lead delivery. The hub 20 need not have any particular minimum or maximum length, although in embodiments configured for medical electrical lead delivery, the overall length of the hub 20 may advantageously be minimized to reduce the required overall length of the lead. In one embodiment, the hub 20 has an overall length, with the actuator in the closed position of from about 2 inches to about 4 inches. In one embodiment, the hub 20 has an overall length with the actuator in the closed position of about 2.25 inches.

The hub 20 may be made from any materials, whether now known or later developed, suitable for use in catheter assemblies, luer hubs, hemostasis valves, and the like. Additionally, the various embodiments of the hub 20 may be manufactured by any methods known in the art for manufacturing similar medical devices and components. In one embodiment, the hub 20 is manufactured by an injection molding process.

As discussed above, in various embodiments of the present invention, the catheter assembly 10 may be used to deliver a medical electrical lead for stimulation of the patient's heart. In one such embodiment, the catheter 14 may be a pre-shaped catheter configured for accessing and cannulating the coronary sinus and branch vessels thereof, and the lead may be of the type configured for stimulating the left side of the heart. In such embodiments, the catheter assembly 10 may first be prepared for catheterization by, for example, flushing the catheter with saline or other suitable material prior to insertion into the patient's vasculature. The distal end of the catheter 14 may then be inserted into the patient's vasculature system through a percutaneous incision into the left subclavian vein, the left auxiliary vein, the left internal or external jugular vein, or the left brachiocephalic vein, and transvenously advanced to the heart according to methods known in the art.

Prior to insertion of the elongate lead through the hub 20, the clinician may first depress the actuator 50 so as to cause the actuator 50 to assume the open position and dilate the seal 56. For example, the actuator 50 may be depressed relative to the housing 40 until resistance is caused by the ribs 240 engaging the actuator retainer member outer edges 350 is felt. In that case, if the depressing force on the actuator 50 is released, the springs 370 will force the actuator 50 back to the closed position. Alternatively, the actuator 50 may be fully advanced distally relative to the housing 40, such that the actuator ribs 240 are positioned distal to the inner edges 354 of the actuator retainer members 70. When the actuator 50 is so positioned, contact between the actuator ribs 240 and the inner edges 354 so as to interfere with spontaneous proximally-directed movement of the actuator 50 relative to the housing 40, effectively locking the actuator 50 in the open position. With the actuator 50 in the open position, the lead may then be inserted through the lumen 76 of the actuator 50 and into the catheter 14. If desired, the actuator 50 may be left locked in the open position as the lead is advanced through the catheter 14 to its implantation position. Alternatively, the actuator 50 may be returned to the closed position by pulling on the actuator 50 to disengage the ribs 240 from the actuator retainer member inner edges 354, in which case the seal 56 can close and seal around the lead as it is advanced through the catheter 14.

With the lead positioned as desired within the patient's vasculature, the catheter 14 may be retracted from the patient without disturbing the position of the lead. As discussed above, because leads often have structures near their proximal ends that are larger in diameter than the catheter lumen, the catheter 14 must be split or cut as it is retracted from the patient's body. Thus, in one embodiment of the present invention, the hub 20 can be split along the break line 38 by, for example, separating (i.e., by pulling apart) the actuator flange 334 at the actuator break line 250 and in turn, splitting or separating the joints 96 connecting the housing elements 84, 88. As discussed above, separating the hub 20 in this manner results in a pair of hub subassemblies contained within the respective housing elements 84, 88. Additionally, as shown above in FIG. 9, separation of the hub 20 exposes the proximal end portion 32 of the catheter 14 coupled to the ferrule 112, thus facilitating cutting the catheter 14 using, for example, one of the cutters described in co-pending and commonly assigned U.S. Patent Application Publication 2005/0182435, and U.S. Provisional Patent Application 60/864,901, entitled "Universal Cutter for Guide Catheters," both of which are incorporated by reference above.

It is emphasized that the type of medical device that can be introduced into the catheter 14 through the hub 20 is not limited to leads. For example, a pre-shaped inner catheter configured for various procedures including, without limitation facilitating subselection of an appropriate branch vessel off of the coronary sinus for left side lead delivery, may be inserted through an outer guide catheter equipped with the hub 20. In another embodiment, the clinician may insert a guidewire through the lumen of the catheter 14 for delivery of an over-the-wire type medical electrical lead or to facilitate further navigation of the catheter 14 or an inner catheter. In other embodiments, other elongate devices may be inserted through the hub 20 and catheter 14 as desired by the clinician. Other procedures and applications utilizing the various hub embodiments described herein will be appreciated by those skilled in the art based on the foregoing.

As discussed above, in other embodiments, the hub 20 according to the various embodiments of the present invention may be utilized in conjunction with devices other than the catheter 14. For example, in one embodiment, an introducer sheath may be coupled at its proximal end to the hub 20, which may provide substantially the same or identical functionality as described herein in connection with the catheter assembly 10. Additionally, the hub 20 may further be used on devices for with procedures relating to regions of the body beyond those described above. For example, the hub 20 may be incorporated into catheters, introducers, or other similar devices used throughout the cardiovascular system, e.g., interventional cardiology procedures within the coronary arterial system, as well as devices utilized for neurostimulation applications and within the gastrointestinal system. Those skilled in the art will recognize other or additional applications of the hub 20 based on the foregoing.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A hemostasis hub for use with a catheter including a lumen and a proximal end, the hemostasis hub comprising:
   a housing including a proximal portion and a distal portion configured to be coupled to the proximal end of the catheter, the housing configured to be splittable or separable along at least one housing break line into first and second housing elements each having a distal end, the at least one housing break line extending generally longitudinally through the proximal and distal portions of the housing, the distal end of the second housing element extending distally with respect to the distal end of the first housing element and operable to support the proximal end of the catheter;
   a hemostasis seal in the proximal portion of the housing; and
   an actuator including a body portion partially slidably disposed within the proximal portion of the housing, a dilator member extending distally from the body portion, and a lumen extending through the body portion and the dilator member, the actuator being separable along an actuator break line generally aligned with the at least one housing break line;
   a spring retainer element disposed within the proximal portion of the housing, the spring retainer element including a tubular spring retainer member; and
   a spring at least partially retained within the spring retainer member,
   wherein the actuator is configured to assume a closed position in which the actuator lumen is fluidly isolated from the catheter lumen by the hemostasis seal, and an open position in which the dilator member extends through the hemostasis seal and the actuator lumen is in fluid communication with the catheter lumen,
   and wherein the hub is configured such that the spring and the spring retainer element are retained within one of the first and second housing elements upon separation of the housing and the actuator.

2. The hemostasis hub of claim 1 wherein the actuator is separable into first and second actuator elements.

3. The hemostasis hub of claim 2 wherein the actuator is configured such that the first and second actuator elements are partially retained, respectively, within the first and second housing elements.

4. The hemostasis hub of claim 2 and further comprising first and second actuator retainer members in the proximal portion of the housing configured to retain the first and second actuator elements, respectively, partially within the first and second housing elements.

5. The hemostasis hub of claim 4 wherein the actuator retainer members are configured to releasably maintain the actuator in the open position.

6. The hemostasis hub of claim 2 wherein the actuator body portion includes a proximal end positioned proximal to the proximal portion of the housing and a distal end disposed within the proximal portion of the housing.

7. The hemostasis hub of claim 6 wherein the spring is configured to bias the actuator to the closed position.

8. The hemostasis hub of claim 7 wherein the actuator body portion includes at least one channel extending proximally from the distal end of the body portion, and wherein the spring is partially received within the channel.

9. The hemostasis hub of claim 8 wherein the spring retainer member is received by the channel of the actuator body portion, wherein the spring is retained within the channel and the spring retainer member.

10. The hemostasis hub of claim 6 and further comprising a plurality of springs retained within the housing configured to bias the actuator to the closed position.

11. The hemostasis hub of claim 10 wherein the actuator body portion includes a pair of channels extending proximally from the distal end of the body portion in each of the first and second actuator elements, and wherein each of the springs is partially retained within one of the channels.

12. The hemostasis hub of claim 11 and further comprising first and second spring retainer elements within the proximal portion of the housing, each of the spring retainer elements including a pair of spring retainer members each received by one of the channels of the actuator body portion, wherein each of the springs is retained within one of the channels and the spring retainer members received therein.

13. The hemostasis hub of claim 12 and further comprising first and second actuator retainer members in the proximal portion of the housing configured to retain the first and second actuator elements, respectively, partially within the first and second housing elements.

14. The hemostasis hub of claim 13 wherein the first housing element is adapted to contain the first actuator retainer member, the first actuator element, and the first spring retainer element, and further wherein the second housing element is adapted to contain the second actuator retainer member, the second actuator element, and the second spring retainer element when the housing is split along the at least one housing break line.

15. The hemostasis hub of claim 1 wherein the seal is a splittable or separable seal, the seal including first and second resilient seal elements.

16. A hemostasis hub for use in combination with a catheter having a proximal end and a lumen extending distally from the proximal end, the hemostasis hub comprising:
   a splittable or separable housing having a proximal portion and a distal portion configured to be coupled to the proximal end of the catheter, the housing defining an interior space, the housing having at least one predetermined housing break line extending generally longitudinally through the proximal and distal portions such that the housing is splittable or separable into first and second housing elements each having a distal end, the distal end of the second housing element extending distally with respect to the distal end of the first housing element and operable to support the proximal end of the catheter;
   a hemostasis seal within the housing;
   an actuator including a body portion partially slidably disposed in the interior space, a dilator member extending distally from the body portion configured to dilate the seal, and an actuator lumen extending through the dilator member, the actuator being splittable or separable along an actuator break line generally aligned with the at least one predetermined housing break line;
   a spring retainer element disposed in the housing having a tubular spring retainer member; and
   a spring disposed within the spring retainer member,
   wherein the hub is configured such that the spring and the spring retainer element are retained within a portion of the housing upon separation of the housing and the actuator.

17. The hemostasis hub of claim 16 wherein the actuator is configured to assume a closed position in which the dilator member is positioned proximal to the hemostasis seal, and an open position in which the dilator member extends through the hemostasis seal such that the actuator lumen is in fluid communication with the catheter lumen.

18. A catheter and hemostasis hub assembly comprising:
   an elongate catheter including a proximal end and a lumen extending distally from the proximal end; and
   a hemostasis hub coupled to the proximal end of the catheter, the hub including:
      a housing defining an interior space in fluid communication with the catheter lumen, the housing including a proximal portion and a distal portion coupled to the proximal end of the catheter, the housing further including first and second housing elements each having a distal end, and at least one predetermined housing break line extending generally longitudinally through the proximal and distal portions, the distal end of the second housing element extending distally with respect to the distal end of the first housing element and operable to support the proximal end of the catheter;
      a resilient seal member within the housing configured to hemostatically isolate the catheter lumen from an open proximal end of the housing; and
      an actuator including mating first and second actuator elements defining an actuator body portion partially slidably disposed within the housing and a dilator extending distally from the body portion configured to dilate the seal for introducing an elongate medical device or instrument into the catheter lumen;
   first and second spring retainer elements each including a tubular spring retainer member; and
   a first spring retained within the spring retainer member of the first spring retainer element, and a second spring retained within the spring retainer member of the second spring retainer element,
   wherein the hub is further configured to be splittable along the at least one predetermined housing break line into a first hub subassembly including the first housing element, the first actuator element, the first spring retainer element, and the first spring, and a second hub subassembly including the second housing element, the second actuator element, the second spring retainer element, and the second spring.

19. The assembly of claim 18 wherein the distal portion of the housing includes an open distal end, and wherein the proximal end of the catheter extends into the open distal end of the housing.

20. The assembly of claim 19 wherein the proximal end of the catheter is releasably coupled to the distal portion of the first housing element, and wherein the proximal end of the catheter is fixedly coupled to the distal portion of the second housing element.

21. The assembly of claim 20 wherein the hub is configured such that upon splitting of the hub, the first hub subassembly is decoupled from the catheter so as to expose the proximal end of the catheter, and the second hub subassembly remains fixedly coupled to the catheter.

* * * * *